United States Patent
Tatara et al.

(10) Patent No.: US 8,382,676 B2
(45) Date of Patent: Feb. 26, 2013

(54) BIOLOGIC INFORMATION DETECTING APPARATUS

(75) Inventors: Naoe Tatara, Musashino (JP); Kimihisa Aihara, Musashino (JP); Shinji Mino, Musashino (JP); Hiroshi Koizumi, Musashino (JP); Shoichi Hayashida, Musashino (JP); Taisuke Oguchi, Musashino (JP); Junichi Shimada, Musashino (JP); Shoichi Sudo, Musashino (JP); Osamu Tochikubo, Kanagawa (JP); Hidetoshi Miura, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 13/183,338

(22) Filed: Jul. 14, 2011

(65) Prior Publication Data

US 2011/0295081 A1  Dec. 1, 2011

Related U.S. Application Data

(62) Division of application No. 11/575,294, filed as application No. PCT/JP2005/018369 on Oct. 4, 2005.

(30) Foreign Application Priority Data

Oct. 6, 2004  (JP) ................... 2004-293238

(51) Int. Cl.
*A61B 5/02*  (2006.01)
(52) U.S. Cl. ....................... 600/485; 600/500
(58) Field of Classification Search .......... 600/323–324, 600/485, 490, 500–504; 381/322, 326, 328, 381/374, 380, 334; 181/129, 130, 135; 379/433.02
See application file for complete search history.

(56) References Cited

U.S. PATENT DOCUMENTS

| | | | |
|---|---|---|---|
| 3,227,155 A | 1/1966 | Erickson et al. | |
| 3,412,729 A | 11/1968 | Smith, Jr. | |

(Continued)

FOREIGN PATENT DOCUMENTS

| | | |
|---|---|---|
| EP | 0923903 A1 | 6/1999 |
| EP | 1217941 | 6/2003 |

(Continued)

OTHER PUBLICATIONS

European office action dated Jun. 9, 2011 for corresponding European application 10005858.5.

(Continued)

*Primary Examiner* — Patricia Mallari
*Assistant Examiner* — Eric Messersmith
(74) *Attorney, Agent, or Firm* — DLA Piper LLP (US)

(57) ABSTRACT

In measurement requiring application of pressure to a tissue of a living body such as blood pressure measurement, noise due to vibration tends to occur. It is therefore difficult to accurately measure a pulse wave and a blood pressure value, and there is a problem of measuring blood pressure stably. It is also difficult to measure blood pressure in daily life activities or to measure blood pressure at predetermined intervals or continuously in a state where a tonometer is always attached. There is consequently a problem of providing a method of holding a biologic information detecting apparatus. The present invention has been achieved to solve the problems and an object of the invention is to provide an easy-to-wear biologic information detecting apparatus for stably detecting biologic information.
In order to achieve the above object, biologic information detecting apparatus according to the invention has a structure in which the apparatus includes a sensor for detecting biologic information in a pair of arms connected via a spindle, and the sensor is tightly attached to a projecting part in a living body, particularly, a tragus of an auricle.

4 Claims, 16 Drawing Sheets

U.S. PATENT DOCUMENTS

| | | | |
|---|---|---|---|
| 3,810,460 A | 5/1974 | Van Nie | 128/2.05 E |
| 4,029,083 A | 6/1977 | Baylor | |
| 4,685,464 A | 8/1987 | Goldberger et al. | |
| 4,730,621 A | 3/1988 | Stott | |
| 5,046,580 A * | 9/1991 | Barton | 181/135 |
| 5,267,566 A | 12/1993 | Choucair et al. | |
| 5,339,810 A | 8/1994 | Ivers et al. | |
| 5,600,730 A * | 2/1997 | Kenning et al. | 381/77 |
| 5,662,104 A | 9/1997 | Fuse et al. | |
| 5,957,840 A | 9/1999 | Terasawa et al. | |
| 5,971,931 A * | 10/1999 | Raff | 600/485 |
| 6,078,829 A | 6/2000 | Uchida et al. | |
| 6,172,743 B1 | 1/2001 | Kley et al. | |
| 6,213,952 B1 | 4/2001 | Finarov et al. | |
| 6,801,798 B2 | 10/2004 | Geddes et al. | |
| 7,341,559 B2 | 3/2008 | Schulz et al. | |
| 7,555,327 B2 | 6/2009 | Matlock | |
| 7,572,227 B2 | 8/2009 | Kondo et al. | |
| 7,572,229 B2 | 8/2009 | Yeo et al. | |
| 7,695,440 B2 | 4/2010 | Kondo et al. | |
| 2002/0173709 A1 | 11/2002 | Fine et al. | |
| 2003/0036690 A1 | 2/2003 | Geddes et al. | |
| 2004/0024326 A1 | 2/2004 | Yeo et al. | |
| 2004/0054291 A1* | 3/2004 | Schulz et al. | 600/500 |
| 2004/0215085 A1* | 10/2004 | Schnall | 600/485 |
| 2007/0073121 A1 | 3/2007 | Hoarau et al. | |
| 2007/0078317 A1 | 4/2007 | Matlock | |
| 2007/0135717 A1 | 6/2007 | Uenishi et al. | |
| 2008/0091112 A1 | 4/2008 | Kondo et al. | |
| 2008/0091113 A1 | 4/2008 | Kondo et al. | |

FOREIGN PATENT DOCUMENTS

| | | |
|---|---|---|
| EP | 1217941 B1 | 6/2003 |
| EP | 1671578 | 6/2006 |
| EP | 1867277 | 12/2007 |
| EP | 1867278 | 12/2007 |
| JP | 48-050580 | 7/1973 |
| JP | 06-055603 | 8/1994 |
| JP | 09-122083 | 5/1997 |
| JP | 10-108845 | 4/1998 |
| JP | 10-108846 | 4/1998 |
| JP | 11-128174 | 5/1999 |
| JP | 3270916 B2 | 1/2002 |
| JP | 2002-238865 | 8/2002 |

OTHER PUBLICATIONS

European office action dated Jun. 9, 2011 for corresponding European application 10005859.3.

European office action dated Jun. 9, 2011 for corresponding European application 10005860.1.

European office action dated Jun. 9, 2011 for corresponding European application 10005861.9.

European office action dated Jun. 9, 2011 for corresponding European application 10005862.7.

Taiwanese language office action dated Sep. 16, 2011 and its English language translation for corresponding Taiwanese application 094134853.

* cited by examiner

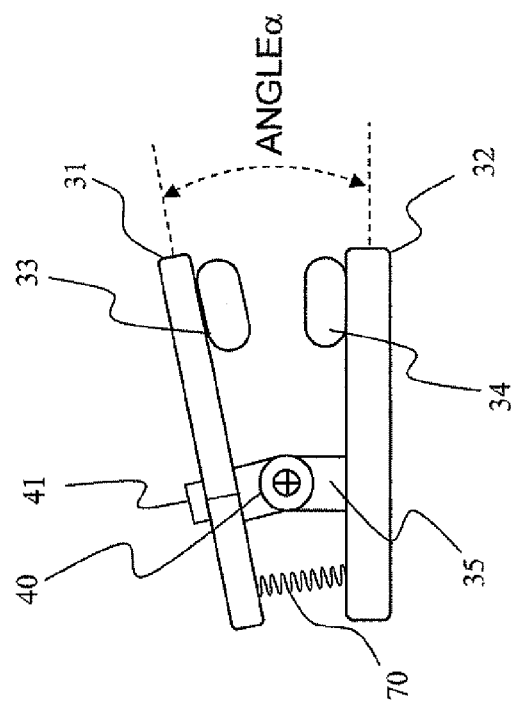
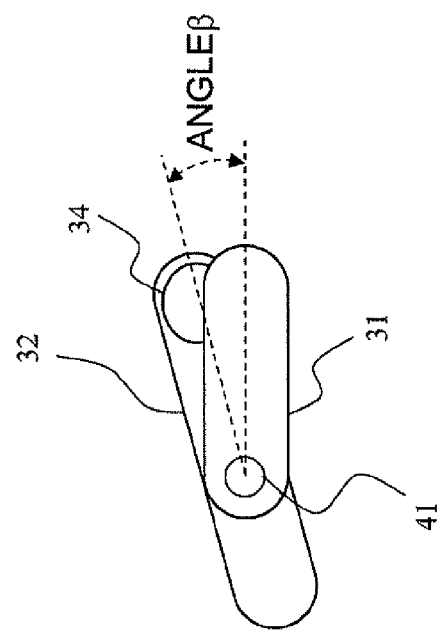
FIG. 1(A)
FIG. 1(B)

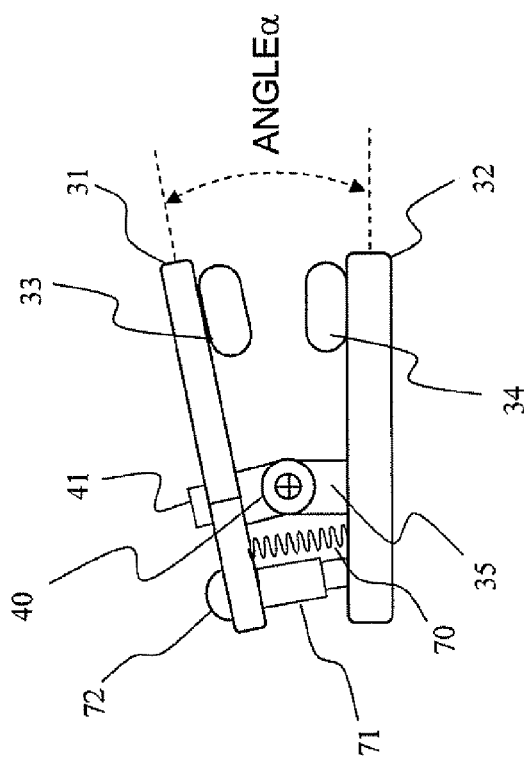 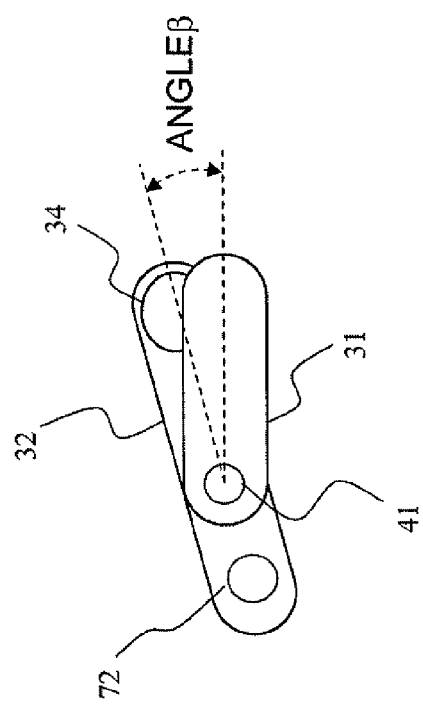
FIG. 2(A)
FIG. 2(B)

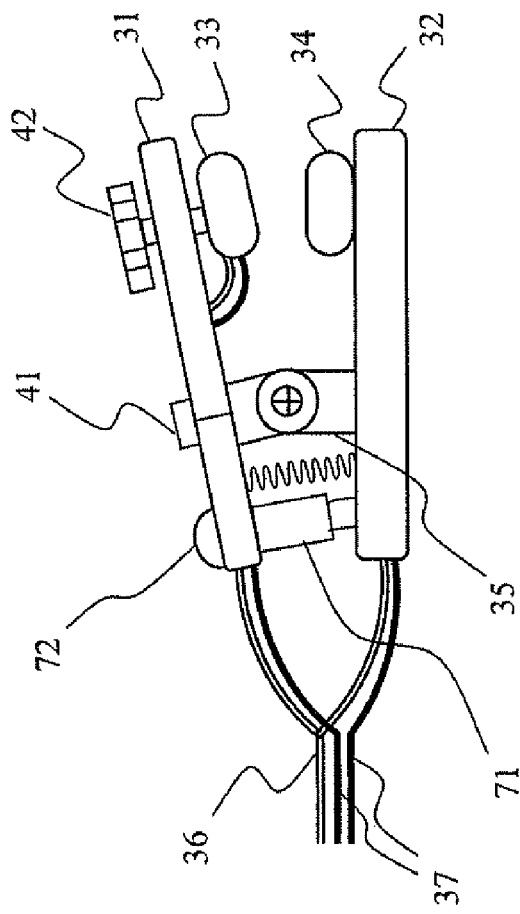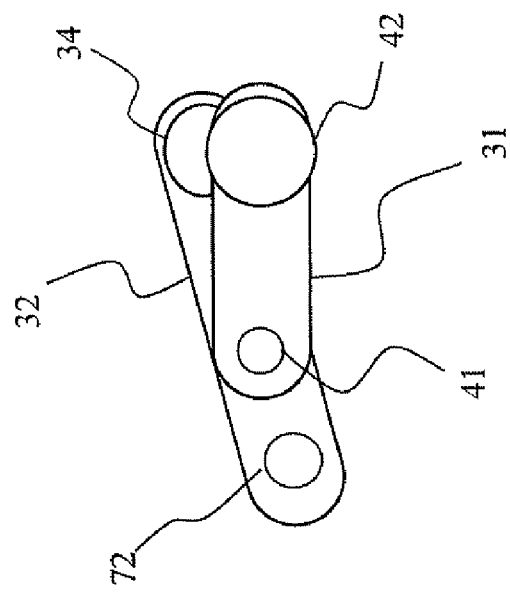
FIG. 4(A)
FIG. 4(B)

US 8,382,676 B2

BIOLOGIC INFORMATION DETECTING APPARATUS

CROSS-REFERENCE TO THE RELATED APPLICATIONS

The present application is a divisional of application Ser. No. 11/575,294, filed on Jan. 16, 2008, which is a national stage of international application No. PCT/JP2005/018369, filed on Oct. 4, 2005, the entire contents of which are incorporated herein by reference. Also, this application claims the benefit of priority under 35 USC 119 to Japanese Patent Application No. 2004-293238, filed on Oct. 6, 2004, the entire contents of which are incorporated herein by reference.

TECHNICAL FIELD

The present invention relates to a biologic information detecting apparatus for detecting biologic information from a part of a living body such as auricle of a human body.

BACKGROUND ART

As the population ages, it is becoming a very important task for the society to address lifestyle-related diseases of adults. In particular, in the case of a disease related to high blood pressure, it is recognized that collection of blood pressure data for a long term is very important. From such a viewpoint, various biologic information detecting apparatuses for detecting blood pressure or the like have been developed.

One of conventional apparatuses for detecting biologic information by using an external ear is a patient monitoring apparatus which is inserted in an ear canal or another region in an external ear and is always attached (refer to, for example, Patent Document 1). Patent Document 1 discloses, as a method of detecting a pulse wave of an artery or a blood flow, a method of emitting light from a light emitting element to a living body, receiving the light scattered by an artery in the living body or a blood cell in an artery by a light receiving element, and detecting a pulse wave or a blood flow from the scattered light. According to the method, pulsation, pulse wave, heart beat, body temperature, arterial oxygen saturation, blood pressure, and the like can be calculated from a light reception amount of scattered light of infrared light or visible light emitted into a living body.

As a device attached to an ear canal or earlobe, there is an emergency information device having radio communication means and including arterial oxygen saturation sensor, a body temperature sensor, a heart beat sensor, and a pulse wave sensor (refer to, for example, Patent Document 2).

On the other hand, with respect to measurement of blood pressure, a blood pressure measuring apparatus using a pulsation waveform of a blood vessel is accepted as one of dominant blood pressure measuring methods besides a blood pressure measuring apparatus (refer to, for example, Non-Patent Document 1) according to a cuff oscillometric method, a volume compensating method, or the like as another method.

In the application, the name of "auricle" is according to Non-Patent Document 2, and the names of auricular cartilages are according to Non-Patent Document 3.

[Patent Document 1] Japanese Patent Application Laid-open No. 9-122083

[Patent Document 2] Japanese Patent Application Laid-open No. 11-128174

[Non-Patent Document 1] Kenichi Yamakoshi and Tatsuo Togawa, "Biologic sensors and measuring apparatuses", edited by Japanese Society for Medical and Biological Engineering (JSMBE), ME textbook series A-1, pp 39 to 52

[Non-Patent Document 2] "Illustrated Human Anatomy Vol. 1 (translation supervisor: Michio Okamoto), Sobotta, p. 126, Igaku-shoin Limited, issued on Oct. 1, 1996

[Non-Patent Document 3] "Illustrated Human Anatomy Vol. 1 (translation supervisor: Michio Okamoto), Sobotta, p. 127, Igaku-shoin Limited, issued on Oct. 1, 1996

DISCLOSURE OF THE INVENTION

Problems to be Solved by the Invention

In measurement requiring application of pressure to a tissue of a living body such as blood pressure measurement, noise due to vibration tends to occur. It is therefore difficult to accurately measure a pulse wave and a blood pressure value, and there is a problem of measuring blood pressure stably. It is also difficult to measure bloodpressure in daily life activities or to measure blood pressure at predetermined intervals or continuously in a state where a tonometer is always attached. There is consequently a problem of providing a method of holding a biologic information detecting apparatus.

The present invention has been achieved to solve the problems and an object of the invention is to provide an easy-to-wear biologic information detecting apparatus for stably detecting biologic information.

Means for Solving the Problems

To achieve the object, a biologic information detecting apparatus according to the present invention has a sensor for detecting biologic information in a pair of arms connected via a spindle. The sensor is tightly attached to a projecting part in a living body, particularly, a tragus of an auricle.

Concretely, a biologic information detecting apparatus according to the present invention includes: a pair of arms that face each other; a spindle connecting the pair of arms at one end of each of the pair of arms; a distance varying mechanism provided for the spindle and adjusting an interval between the other ends of the pair of arms; a sensor for detecting biologic information, which is attached to the other end of at least one of the pair of arms and attached on the facing sides of the pair of arms; and an extensible member for shortening the interval between the other ends of the pair of arms.

The interval between the other ends of the pair of arms can be adjusted by the distance varying mechanism provided for the spindle, and the sensor attached to the arm can be tightly attached to a living body by the extensible member that shortens the interval between the other ends.

A biologic information detecting apparatus according to the invention includes: a pair of arms that face each other; a spindle connecting the pair of arms at one end of each of the pair of arms; a distance varying mechanism provided for the spindle and adjusting an interval between the other ends of the pair of arms; a sensor for detecting biologic information, which is attached to the other end of at least one of the pair of arms and attached on the facing sides of the pair of arms; and a latch for temporarily regulating widening of the interval between the other ends of the pair of arms.

The interval between the other ends of the pair of arms can be adjusted by the distance varying mechanism provided for the spindle, and close attachment to a living body of the sensor attached to the arm can be continued by the latch for temporarily regulating widening of the interval between the other ends.

In the biologic information detecting apparatus according to the present invention, the sensor may be mounted at a tip of an adjusting screw attached to a screw hole penetrating the other end of the arm.

By mounting the sensor at the tip of the adjusting screw, the degree of close attachment to a living body can be adjusted.

In the biologic information detecting apparatus according to the invention, the sensor may be a light emitting element for emitting output light to a living body such as an auricle, and a light receiving element for receiving the output light from the light emitting element, which is scattered by the living body, or passed through the living body.

By making output light of the light emitting element enter a living body and receiving light scattered by the living body or light passed through the living body by the light receiving element, biologic information can be obtained. For example, a pulse wave can be detected.

In the biologic information detecting apparatus according to the invention, the sensor may be a cuff for applying pressure to a living body and detecting pressure from the living body.

By measuring a small pressure fluctuation in the cuff while applying pressure to a living body by the cuff, a pressure pulse wave from the living body can be detected.

The biologic information detecting apparatus according to the invention may further include a cuff for pressing a living body, which is attached to the other end of at least one of the pair of arms and attached on the facing sides of the pair of arms, and the sensor may be provided in the cuff.

By providing the sensor in the cuff, biologic information in a living body part pressed by the cuff can be obtained. In addition, the size of the biologic information detecting apparatus can be reduced.

A biologic information detecting apparatus according to the present invention includes: a pair of arms that face each other; a spindle connecting the pair of arms at one end of each of the pair of arms; a distance varying mechanism provided for the spindle and adjusting an interval between the other ends of the pair of arms; and a cuff for pressing a living body, which is attached to the other end of at least one of the pair of arms and attached on the facing sides of the pair of arms, and is characterized in that an arm to which the cuff is attached or a frame surrounding the cuff comes into contact with a living body in a state where air is exhausted from the cuff and, the cuff comes into contact with a living body surface and presses a tragus in a state where air is supplied to the cuff.

The interval between the other ends of the pair of arms can be adjusted by the distance varying mechanism provided for the spindle. By reducing the pressure in the cuff, the cause of error in measurement due to pressurization can be eliminated.

A biologic information detecting apparatus according to the invention includes: a pair of arms that face each other; a spindle connecting the pair of arms at one end of each of the pair of arms; a distance varying mechanism provided for the spindle and adjusting an interval between the other ends of the pair of arms; and a cuff for pressing a living body, which is attached to the other end of at least one of the pair of arms and attached on the facing sides of the pair of arms, and is characterized in that at least the cuff is detachable from an arm to which the cuff is attached.

The interval between the other ends of the pair of arms can be adjusted by the distance varying mechanism provided for the spindle, and replacement of a dirty or worn cuff and sanitary management is facilitated.

A biologic information detecting apparatus according to the invention includes: a pair of arms that face each other; a spindle connecting the pair of arms at one end of each of the pair of arms; a distance varying mechanism provided for the spindle and adjusting an interval between the other ends of the pair of arms; and a cuff for pressing a living body, which is attached to the other end of at least one of the pair of arms and attached on the facing sides of the pair of arms, and is characterized in that at least one of the cuffs can vary a direction in which the cuff comes into contact with the living body.

The interval between the other ends of the pair of arms can be adjusted by the distance varying mechanism provided for the spindle, and the degree of close attachment to a living body can be increased by varying the direction of the cuff.

A biologic information detecting apparatus according to the invention includes: a pair of arms that face each other; a spindle connecting the pair of arms at one end of each of the pair of arms; a distance varying mechanism provided for the spindle and adjusting an interval between the other ends of the pair of arms; and a cuff for pressing a living body, which is attached to the other end of at least one of the pair of arms and attached on the facing sides of the pair of arms, and is characterized in that at least one of the cuffs can slide in a long axis direction of an arm to which the cuff is attached.

The interval between the other ends of the pair of arms can be adjusted by the distance varying mechanism provided for the spindle, and the cuff can be slid to an optimum position in a living body.

The biologic information detecting apparatus according to the invention may further include an extensible member for moving the cuff toward the other end of the arm to which the cuff is attached.

By pushing the cuff toward the other end of the arm, the cuff can be closely attached to a living body.

The biologic information detecting apparatus according to the invention is characterized by further including a rotating mechanism for rotating at least one of the pair of arms around the spindle as a center axis.

Even in the case where the shape of a living body is complicated, the cuff can be closely attached to the living body by changing the angle formed between the arms.

In the biologic information detecting apparatus according to the invention, the pair of arms sandwiches a projecting part of an auricle in a human body by an arm disposed on one of side face sides of the projecting part of the auricle in the human body and an arm disposed on the other side face side of the projecting part of the auricle in the human body.

By sandwiching the projecting part of an auricle by the pair of arms, the biologic information detecting apparatus can be attached to the auricle.

In the biologic information detecting apparatus according to the invention, the pair of arms sandwiches a tragus as a projecting part of an auricle in the human body by an arm disposed on one of side face sides of the tragus as the projecting part of the auricle in the human body and an arm disposed on the other side face side of the tragus as the projecting part of the auricle in the human body.

By sandwiching a tragus by the pair of arms, the biologic information detecting apparatus can be attached to the auricle.

The biologic information detecting apparatus according to the invention is characterized by further including an ear attachment that is placed around the base of an auricle in a human body.

The biologic information detecting apparatus can be stably attached to an auricle.

The biologic information detecting apparatus according to the invention is characterized by further comprising: a cushion provided on an auricle side of an arm disposed on the auricle side in the pair of arms; a magnet provided for at least one of the arm provided with the cushion and the ear attachment; and a magnet or a magnetic member provided for the other one of the arm and the ear attachment.

By providing the cushion, the biologic information detecting apparatus can be worn for long time. Since the ear attachment and the cushion attract each other because of the magnetic forces, noise caused by body movement can be reduced.

The biologic information detecting apparatus according to the invention is characterized by further including: a bridge connecting the pair of arms attached to one of right and left auricles of a human body and the other auricle to which the pair of arms is not attached; and a power supply unit disposed in some midpoint of the bridge and driving the sensor.

By providing the bridge extended between the right and left auricles, the biologic information detecting apparatus can be stably attached to the auricle. By providing the power supply unit separately from the arm, the weight of the arm can be reduced.

The biologic information detecting apparatus according to the invention is characterized by further including: an ear attachment which is hung from the base of an auricle of a human body; and a power supply unit disposed in the ear attachment.

By providing the ear attachment, the biologic information detecting apparatus can be stably attached to an auricle. By disposing the power supply unit in the ear attachment, the load on the arm is lessened, and noise caused by vibration of a wire can be reduced.

Effect of the Invention

The biologic information detecting apparatus of the present invention is easy to wear and can stably detect biologic information.

BRIEF DESCRIPTION OF THE DRAWINGS

FIG. 1(A) is a front view showing a configuration example of a biologic information detecting apparatus of an embodiment of the present invention, and FIG. 1(B) is a plan view showing a configuration example of the biologic information detecting apparatus of the embodiment.

FIG. 2(A) is a front view showing a configuration example of the biologic information detecting apparatus of the embodiment, and FIG. 2(B) is a plan view showing a configuration example of the biologic information detecting apparatus of the embodiment.

FIG. 4(A) is a front view showing a configuration example of the biologic information detecting apparatus of the embodiment, and FIG. 4(B) is a plan view showing a configuration example of the biologic information detecting apparatus of the embodiment.

Figure 3A:
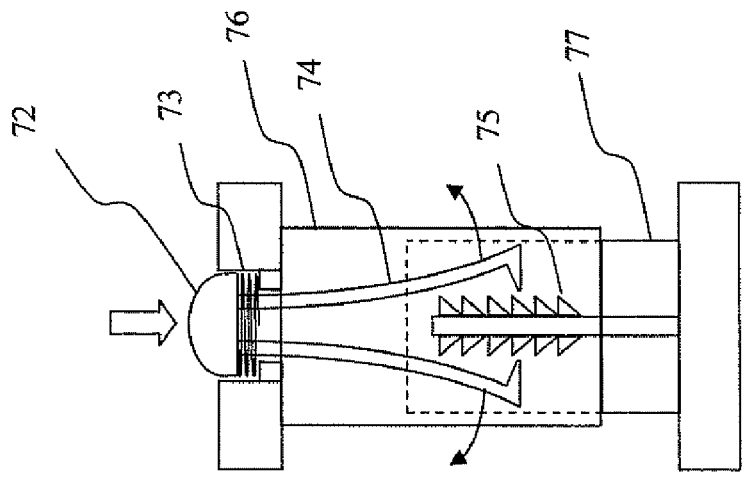
FIG. 3 is a diagram showing a latch mechanism of the biologic information detecting apparatus of the embodiment.

DESCRIPTION OF REFERENCE NUMERALS 1 tragus
2 antitragus
3 concha auriculae
4 antihelix
5 helix
6 crus anthelicis
7 crus helicis
8 cavity of the concha
30 biologic information detecting apparatus
31 first arm
32 second arm
33 sensor
34 sensor
35 spindle
36 air pipe
37 signal line
40 distance varying mechanism
41 rotating mechanism
42 adjustment screw
45 cushion
46 ear attachment mechanism
47 magnet
48 magnet
55 cuff
56 cuff
57 supporting member
61 light emitting element
62 light receiving element
70 spring
71 latch mechanism
72 latch opening button
73 coil spring 74 plate spring
75 nail for latch
76 supporting member A
77 supporting member B
80 bridge
82 power supply unit
83 switches
84 pump
86 sealing member
88 cuff rotating mechanism
90 cuff sliding mechanism

BEST MODE FOR CARRYING OUT THE INVENTION

Embodiments of a biologic information detecting apparatus of the invention will be described with reference to the appended drawings. The invention is not limited to the following embodiments.

Figure 16:
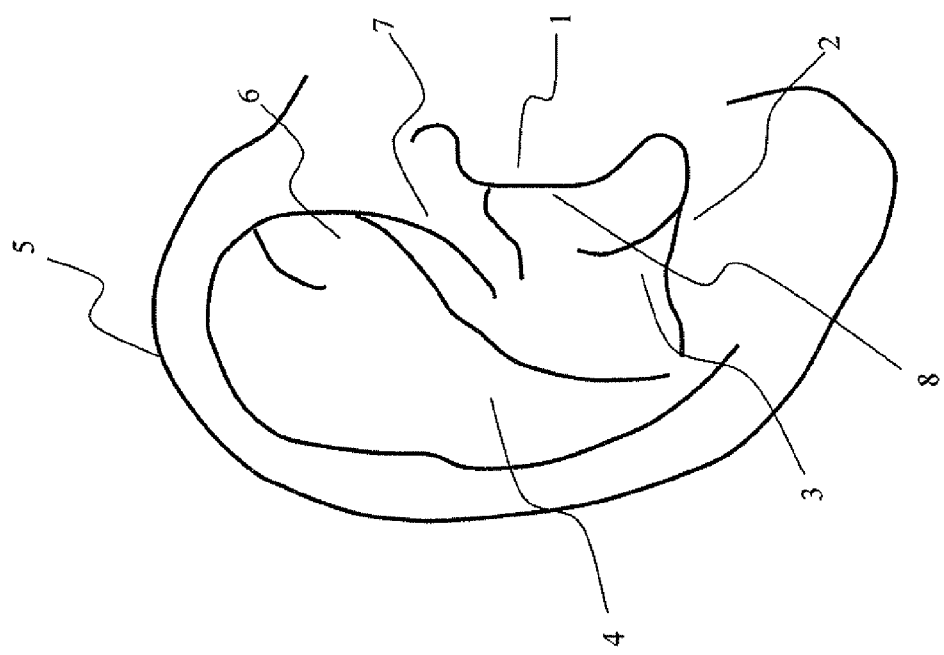
FIG. 16 is a diagram showing names of parts in an auricle.

In the application, "the inside of a tragus" is the side of a cavity of the concha 8 of a tragus 1 in FIG. 16. "The outside of a tragus" is the side opposite to the cavity of the concha 8 in FIG. 16.

(First Embodiment)

A biologic information detecting apparatus of a first embodiment has a pair of arms that face each other, a spindle connecting the pair of arms at one end of each of the pair of arms, a distance varying mechanism provided for the spindle and adjusting the interval of the other ends of the pair of arms, a sensor for detecting biometric information, attached to the other end of at least one of the pair of arms and attached on the facing sides of the pair of arms, and an extensible member for shortening the interval between the other ends of the pair of arms.

The biologic information detecting apparatus may further include a rotating mechanism for rotating at least one of the pair of arms around the spindle as a center axis.

FIG. 1(A) is a front view showing a configuration example of a biologic information detecting apparatus of the embodiment, and FIG. 1(B) is a plan view showing a configuration example of the biologic information detecting apparatus of the invention. The biometric information detecting apparatus shown in FIGS. 1(A) and 1(B) has a distance varying mechanism 40 for adjusting the interval between other ends facing each other of a first arm 31 and a second arm 32, for example, in a portion in which the first and second arms 31 and 32 are connected to a spindle 35 or to the spindle 35. The distance varying mechanism 40 has the function of adjusting the interval between facing surfaces of the first and second arms 31 and 32 by changing the angle formed between the spindle 35 and the first arm 35, thereby changing an angle α shown in FIG. 1(A).

As the mechanism of varying the angle of the distance varying mechanism 40, a mechanism of adjusting the angle between the spindle 35 and the first arm 31 by a screw, a mechanism using both friction and screwing, or the like maybe used. Further, as the mechanism of adjusting the interval between the facing other ends of the first and second arms 31 and 32, a mechanism of adjusting the length of the spindle 35 may be used.

The biologic information detecting apparatus shown in FIG. 1(A) has, in its part in which the first arm 31 and the spindle 35 are connected to each other, a rotating mechanism 41 which is obtained by breaking the tip of the spindle 35 of the first arm 31 and moves the spindle 35 in the rotating direction. The rotating mechanism 41 has the function of varying an angle β formed between the direction of the first arm 31 and the direction of the second arm 32 viewed from the axial direction of the spindle 35 shown in FIG. 1(B). It is option to provide the rotating mechanism 41.

In the case of the configuration example of the biologic information detecting apparatus shown in FIGS. 1(A) and 1(B), a spring 70 for shortening the interval between the other end of the first arm 31 and the other end of the second arm 32 is provided.

The spring 70 shown in FIG. 1(A) works so as to shorten the interval between the other end of the first arm 31 and the other end of the second arm 32. For example, the interval between sensors 33 and 34 is widened by pinching one end of the first arm 31 and one end of the second arm 32 to sandwich a living body and the spring 70 is released. By the stretching force of the spring 70, the sensors 33 and 34 are tightly attached to the living body.

When the spring 70 is disposed to the other end side more than the spindle 35, the interval between the sensors 33 and 34 is widened by pinching one end of the first arm 31 and one end of the second arm 32 to sandwich a living body and the spring 70 is released. By the tensile force of the spring 70, the sensors 33 and 34 are tightly attached to the living body.

Although a coil spring is used as an example of the extensible member, the invention is not limited to the coil spring. Any extensible member such as a plate spring, a torsion spring, an air spring, rubber, resin, or the like may be used.

The biologic information detecting apparatus has the function of detecting biologic information in a state where the sensors 33 and 34 are in contact with a part of a projection of an auricle of a human body, for example, on both sides of a tragus of an auricle. In the case where the sensors 33 and 34 are in contact with a tragus from both sides, the interval between the sensors 33 and 34 is adjusted to a proper contact state by the distance varying mechanism 40 by changing the distance between facing surfaces of the first and second arms 31 and 32. Further, the contact positions of the sensors 33 and 34 are adjusted to proper positions by changing the angle β shown in FIG. 1(B) by the rotating mechanism 41. After adjustment, the interval between the other end of the first arm 31 and the other end of the second arm 32 is shortened by the spring 70, so that the sensors 33 and 34 can be tightly attached to the living body.

As described above, in the biologic information detecting apparatus of the embodiment, the interval between the other ends of the pair of arms can be adjusted by the distance varying mechanism provided for the spindle, and the sensors attached to the arms can be tightly attached to a living body by the extensible member that shortens the interval between the other ends of the arms. By the rotating mechanism that rotates the arms, even in the case where the shape of a living body is complicated, the cuffs can be tightly attached to the living body by changing the angle formed by the arms. Therefore, biologic information can be stably detected by the small and light apparatus which can be attached in a proper position with a proper contact pressure in accordance with the shape of an individual.

(Second Embodiment)

A biologic information detecting apparatus of a second embodiment has a pair of arms that face each other, a spindle connecting the pair of arms at one end of each of the pair of arms, a distance varying mechanism provided for the spindle and adjusting the interval of the other ends of the pair of arms, a sensor for detecting biometric information, attached to the other end of at least one of the pair of arms and attached on the facing sides of the pair of arms, and a latch for temporarily regulating widening of the interval between the other ends of the pair of arms.

FIG. 2(A) is a front view showing a configuration example of the biologic information detecting apparatus of the second embodiment, and FIG. 2(B) is a plan view showing a configuration example of the biologic information detecting apparatus of the second embodiment. In the case of the configuration example of the biologic information detecting apparatus shown in FIGS. 2(A) and 2(B), the spring 70 for shortening the interval between the other end of the first arm 31 and the other end of the second arm 32 is provided and, in addition, a latch mechanism 71 for preventing the interval between the other end of the first arm 31 and the other end of the second arm 32 from widening is also provided.

The spring 70 shown in FIG. 2(A) works in the direction of widening the interval between one end of the first arm 31 and one end of the second arm 32. For example, the interval between sensors 33 and 34 is widened by pinching one end of the first arm 31 and one end of the second arm 32 to sandwich a living body and the spring 70 is released. The sensors 33 and 34 are tightly attached to the living body. The latch mechanism 71 maintains the state where the sensors 33 and 34 are tightly attached to the living body.

Figure 3B:
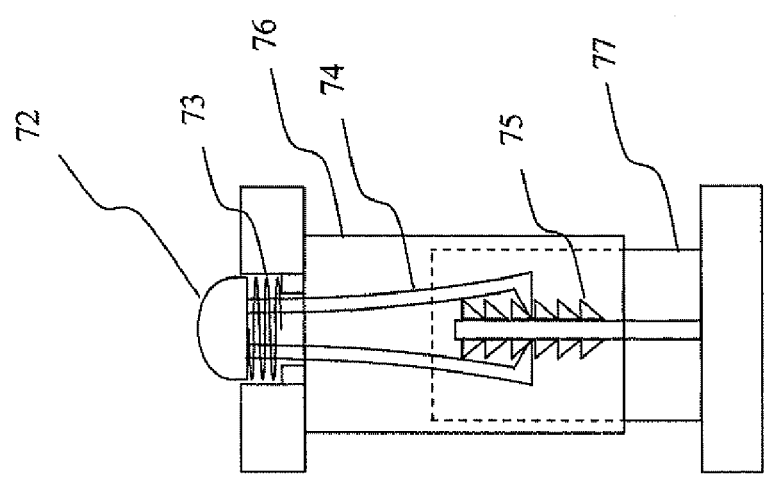

The latch mechanism will be described with reference to FIG. 3. In FIG. 3, 72 denotes a latch unlock button, 73 denotes a coil spring, 74 denotes a plate spring, 75 denotes a nail for latch, 76 denotes a supporting member A, and 77 indicates a supporting member B. FIG. 3(A) shows a state where the latch mechanism is locked, and FIG. 3(B) shows a state where the latch mechanism is released. In FIG. 3(A), the plate spring 74 is temporarily retained by the nail 75 for latch, thereby regulating entrance of the supporting member B 77 to the supporting member A 76. In this state, in FIG. 3(A), widening of the interval between the first and second arms 31 and 32 is regulated. That is, it suppresses dropping of the biologic information detecting apparatus once sandwiching the living body.

As shown in FIG. 3(B), when the latch unlock button 72 is depressed, the plate spring 74 is opened in the direction shown by the arrows and released from the nails 75 for latch. When the plate spring 74 caught by the coil spring 73 is released from the nails 75 for latch, the supporting member B 77 can enter the supporting member A 76. In this state, in FIG. 3(A), the interval between the first and second arms 31 and 32 is widened. That is, the biologic information detecting apparatus which has once sandwiched a living body can be easily detached.

As described above, in the biologic information detecting apparatus of the invention, the interval between the other ends of the pair of arms can be adjusted by the distance varying mechanism provided for the spindle, and close attachment of the sensors attached to the arms to a living body can be continued by the latch that temporarily regulates widening of the interval between the other ends of the pair of arms. Consequently, biologic information can be detected by the small and light apparatus which can be stably attached in a proper position with a proper contact pressure in accordance with the shape of an individual.

(Third Embodiment)

A biologic information detecting apparatus of a third embodiment is similar to the above-described biologic information detecting apparatus except that an adjusting screw on which a sensor is mounted or an adjusting screw on which a sensor is mounted and which has the function of adjusting at least one of the interval between the sensor and the surface of the first arm, and the interval between the sensor and the surface of the second arm is provided for the first arm and/or the second arm.

FIG. 4(A) is a front view showing a configuration example of the biologic information detecting apparatus of the embodiment, and FIG. 4(B) is a front view showing a configuration example of the biologic information detecting apparatus of the embodiment. In FIG. 4 and subsequent diagrams, in order to avoid complication of the drawings, indication of names of part of the components is not shown. In the configuration example of the biologic information detecting apparatus shown in FIGS. 4(A) and 4(B), in the biologic information detecting apparatus, the first arm 31 has an adjusting screw 42, the sensor 33 is mounted on the adjusting screw 42, and the interval between the sensor 33 and the sensor 34 provided for the second arm 32 is adjusted by the adjusting screw 42. It is optional to provide a rotating mechanism and a latch mechanism.

The mechanism of the adjusting screw 42 may be a mechanism for adjusting the interval between the sensors 33 and 34 by adjusting the position of the sensor 33 by rotating a screw or a mechanism for adjusting the interval between the sensors 33 and 34, by adjusting the position of the sensor 33 by friction and fixing the position by a fixing screw.

As described above, in the case of attaching the biologic information detecting apparatus of the embodiment on, for example, a tragus of an auricle, the interval between the sensors 33 and 34 is finely adjusted by an adjusting screw in accordance with an individual difference of the shape of the tragus, so that the sensors 33 and 34 can be attached to the tragus with proper contact pressure.

In the following embodiment, the tragus of the auricle will be described as an example of the projection of the auricle of a human body.

(Fourth Embodiment)

Figure 5:
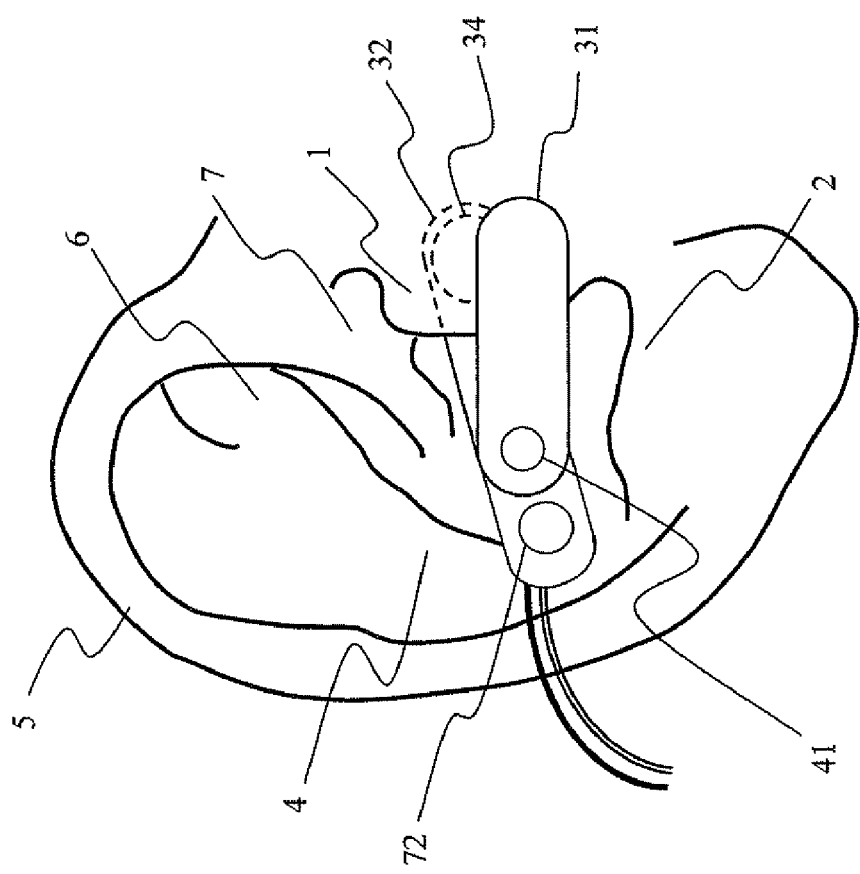
FIG. 5 is a diagram showing an example of attachment of the biologic information detecting apparatus of the embodiment to an auricle.

FIG. 5 shows an example of attachment of the biologic information detecting apparatus to an auricle. In FIG. 5, the biologic information detecting apparatus is attached so as to come into contact with the tragus 1 from both sides so that the sensor 33 of the first arm 31 is in contact with the outside of the tragus 1, and the sensor 34 of the second arm 32 is in contact with the inside of the tragus 1. Since part of the second arm 32 and the sensor 34 are on the inside of the tragus 1, they are shown by broken lines.

As described above, in the case of detecting biologic information in a state where the biologic information detecting apparatus of the embodiment is attached to a part of a living body, for example, on both sides of the tragus 1 of an auricle, the positions of the sensors 33 and 34 are adjusted by the distance varying mechanism 40 or the rotating mechanism 41 in correspondence with the individual difference of the shape of the tragus 1. Therefore, the sensors 33 and 34 can be attached in a proper position in the tragus 1 in a proper contact state. It is option to provide the rotating mechanism and the latch mechanism.

(Fifth Embodiment)

Figure 6B:
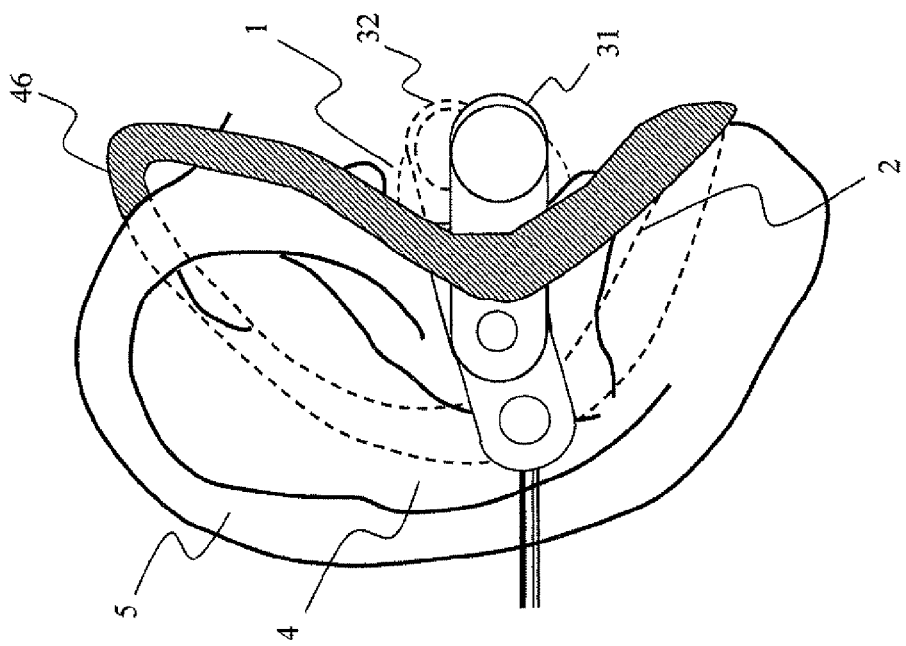
FIG. 6(B) shows a state where the biologic information detecting apparatus of the embodiment is attached to the auricle.
Figure 6A:
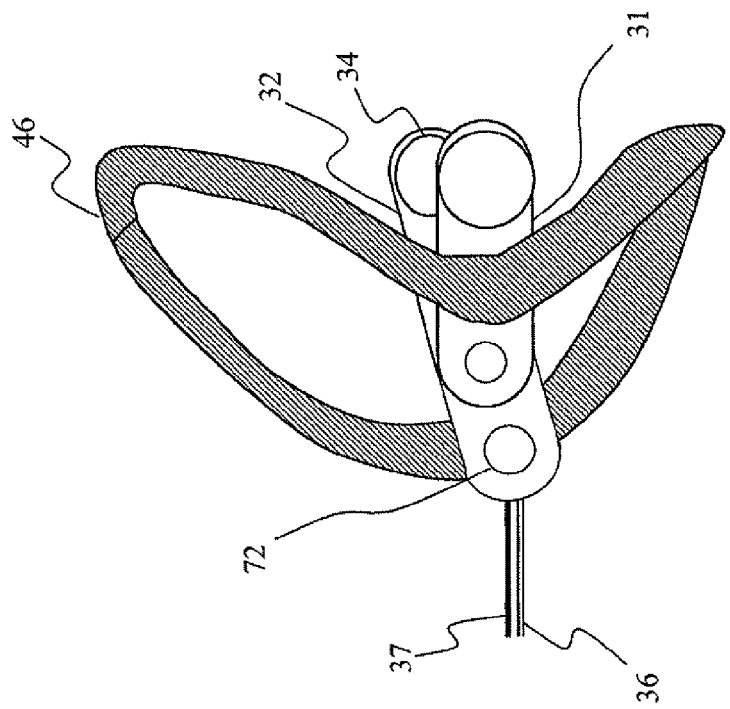
FIG. 6(A) is a diagram showing a configuration example of the biologic information detecting apparatus of the embodiment.

A biologic information detecting apparatus of a fifth embodiment relates to the case where the above-described biologic information detecting apparatus further has an ear attachment part that surrounds the base of an auricle. FIG. 6(A) shows a configuration example of the biologic information detecting apparatus of the fifth embodiment, and FIG. 6(B) shows a state where the biologic information detecting apparatus of the embodiment is attached to the auricle. In the case of the configuration example of the biologic information detecting apparatus shown in FIG. 6(A), the first arm 31 has an ear attachment mechanism 46. The ear attachment mechanism 46 is a mechanism for fixing the biologic information detecting apparatus to the auricle by being extended from the base of the auricle to the back side of a helix 5 so as to surround the base of the auricle as shown in FIG. 6(B).

The ear attachment may have a ring shape extending along an auricle. The ear attachment mechanism may have a structure that surrounds the base of an auricle and its ring shape is closed by a hook. Further, the degree of closing of the closed ring may be adjusted with a stopper.

The material of the ear attachment maybe a metal having plasticity, solder alloy, zinc alloy, brass, copper alloy, aluminum alloy, stainless steel, Ni alloy, tin alloy, or shape memory alloy. As resin materials, plastics, polyvinyl chloride resin, acrylic resin, ABS resin, MC nylon, fluororesin (PTFE), polycarbonate, polypropylene, polyethylene silicone resin, polyurethane resin, or natural rubber may be used. By selecting such materials, the individual differences such as the size of an auricle of a subject can be absorbed.

As described above, the biologic information detecting apparatus of the embodiment has the ear attachment mechanism 46 which hangs on an auricle so as to surround the base of the auricle, so that a deviation from the position of the tragus of the apparatus due to the dead load of the apparatus or the motion of the subject can be prevented. Thus, the biologic information detecting apparatus is stably fixed to the auricle, and biologic information can be detected more stably.

The ear attachment mechanism 46 may have a structure which is detachable from the body of the biologic information apparatus, and the ear attachment mechanism 46 of a size adapted to the subject can be selected.

(Sixth Embodiment)

A biologic information detecting apparatus of a sixth embodiment is obtained by further providing the above-described biologic information detecting apparatus with a cushion provided on the auricle side of an arm disposed on the auricle side of the pair of arms, a magnet provided for at least one of the arm provided with the cushion and the ear attachment, and a magnet or a magnetic member provided for the other one of them.

Figure 7:
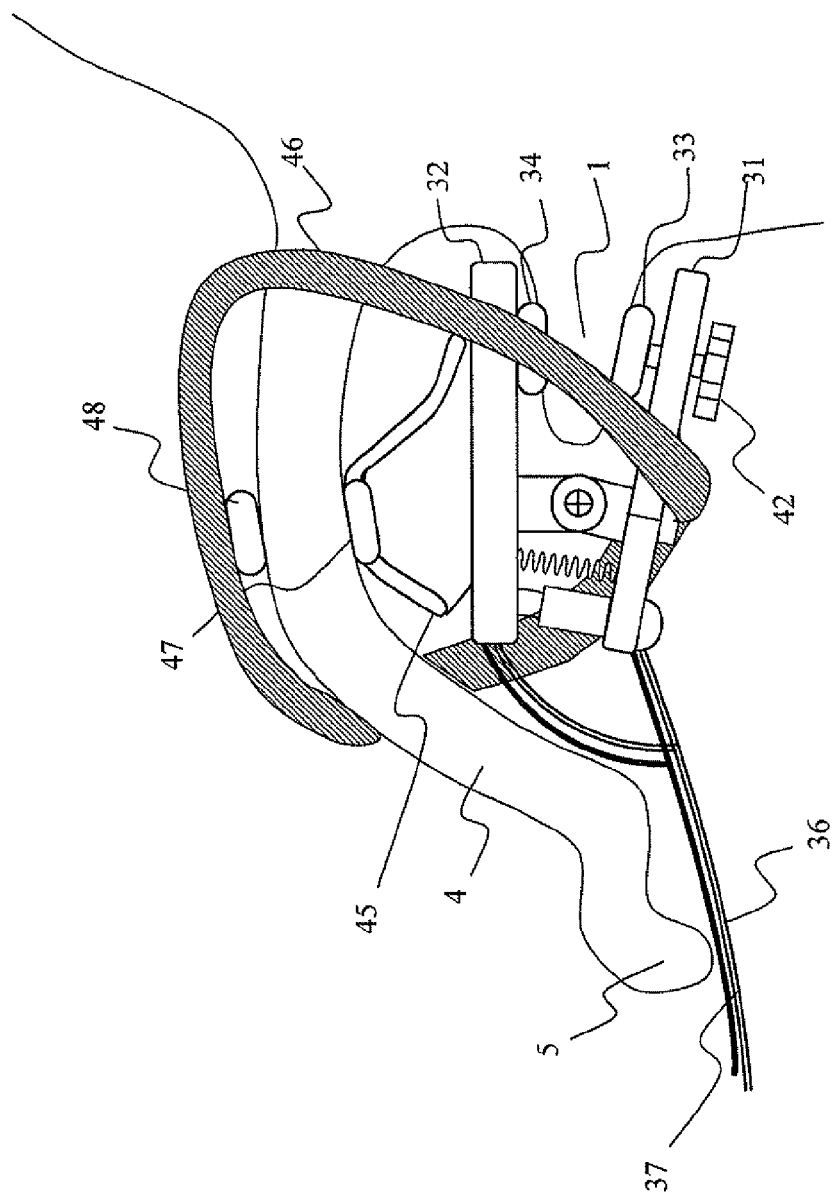
FIG. 7 is a diagram showing a state where the biologic information detecting apparatus of the embodiment is supposedly attached to the auricle.

FIG. 7 is a diagram showing a state where the biologic information detecting apparatus of the sixth embodiment is supposedly attached to the auricle. FIG, 7 is a schematic diagram in which the auricle is shown in section along a horizontal plane near the tragus 1 viewed from above the head of a living body, and an attachment state of the biologic information detecting apparatus to the living body is viewed from above the head of the living body. In FIG. 7, a cushion 45 is disposed on the outside of the second arm 32. The cushion 45 has a magnet 47 in a position in contact with the auricle. The ear attachment mechanism 46 has a magnet 48 in a position in contact with the auricle on the back side of the auricle.

The magnets 47 and 48 are on both sides of an antihelix 4 of the auricle and have polarities so that magnetic forces of the magnets 47 and 48 act each other. The magnets 47 and 48 are fixed in contact with the auricle.

As described above, by providing the cushion 45, even in the case where the arm in the biologic information detecting apparatus is made of a hard material, the apparatus can be attached for long time without giving pain to the subject . In the biologic information detecting apparatus of the embodiment, the cushion 45 further includes the magnet on the side in contact with the auricle, and the ear attachment mechanism 46 further includes the magnet on the side in contact with the auricle so that their magnetic forces act each other. The biologic information detecting apparatus is fixed to the auricle more comfortably, and biologic information can be detected more stably.

Although the two magnets 47 and 48 are used in FIG. 7, one magnet and a magnetic member instead of the other magnet may be used. The magnets 47 and 48 may be provided in the cushion 45 and the ear attachment mechanism 46, respectively.

As described above, the biologic information detecting apparatus of the embodiment which is small and light can be attached more comfortably to a tragus of a living body in a proper position with a proper contact pressure in correspondence with variations in the body shape of an individual, and can detect biologic information more stably and continuously.

(Seventh Embodiment)

In a biologic information detecting apparatus of a seventh embodiment, the body of the above-described biologic information detecting apparatus is attached to one of right and left auricles of a human body, and the apparatus further includes a bridge connecting the pair of arms and an auricle to which the pair of arms is not attached, and a power supply unit disposed in some midpoint of the bridge and driving a sensor.

Figure 8:
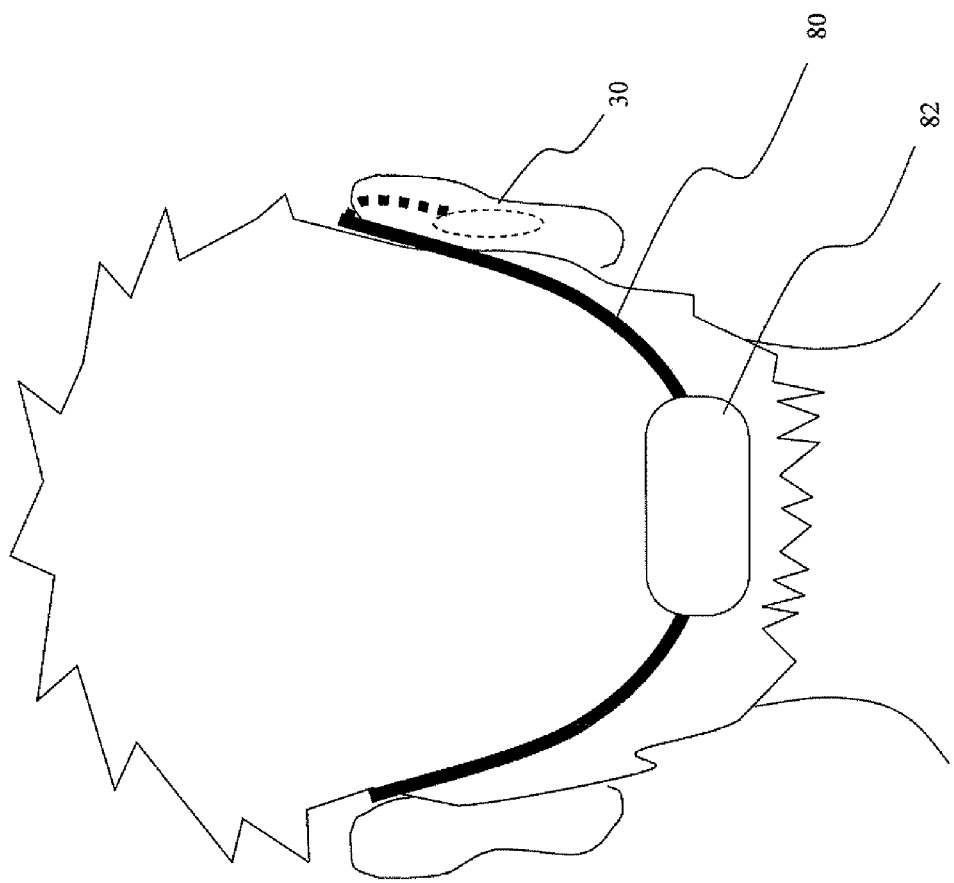
FIG. 8 is a diagram showing an attachment state of the biologic information detecting apparatus of the embodiment.

FIG. 8 shows an attachment state of the biologic information detecting apparatus of the seventh embodiment. In FIG. 8, 30 denotes a biologic information detecting apparatus, 80 denotes a bridge, and 82 indicates a power supply unit . In the case of the configuration example of the biologic information detecting apparatus shown in FIG. 8, the body of the biologic information detecting apparatus is attached to one of the right and left auricles of a human body, and a power supply unit for driving a sensor is disposed in a bridge connecting the pair of arms and the auricle to which the pair of arms is not attached via the back part of the head of the human body. In the case where a cuff is provided for the pair of arms, a pump for supplying/exhausting air to/from the cuff and also to the power supply unit may be disposed.

The material of the bridge maybe a metal having plasticity, solder alloy, zinc alloy, brass, copper alloy, aluminum alloy, stainless steel, Ni alloy, tin alloy, or shape memory alloy. As resin materials, plastics, polyvinyl chloride resin, acrylic resin, ABS resin, MC nylon, fluororesin (PTFE), polycarbonate, polypropylene, polyethylene silicone resin, or polyurethane resin may be used. By selecting such materials, the individual differences such as the size of the head of a subject can be absorbed.

The bridge may have a structure that can be detached from the body of the biologic information detecting apparatus, and a bridge of a size adapted to the subject can be selected. The bridge may be formed extensibly so as to be adapted to the size of the head of a subject.

Although the bridge extends along the back part of the head, the bridge may extend along the top of the head or the under the chin.

By disposing the power supply unit on the head, portability and management of the biologic information detecting apparatus can be facilitated. By disposing the pump on the head, a pipe can be easily fixed and noise can be reduced at the time of detection of biologic information.

As described above, by providing the bridge extending across the right and left auricles, the biologic information detecting apparatus can be stably attached to the auricle. By providing the power supply unit separately from the arm side, the weight of the arm side can be reduced.

(Eighth Embodiment)

Figure 9A:
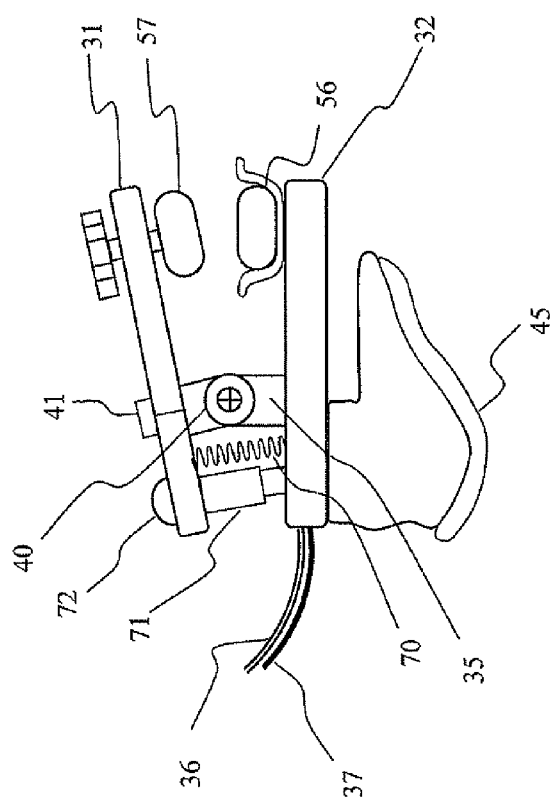
FIG. 9(A) shows a configuration example of the biologic information detecting apparatus of the embodiment.
Figure 9B:
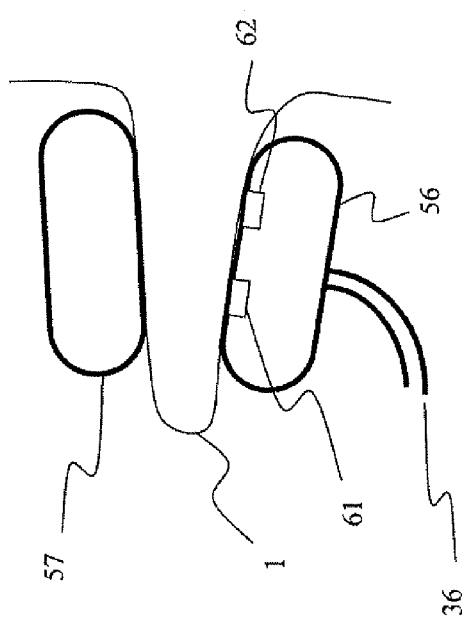
FIG. 9(B) is an enlarged view of a portion of a supporting member and a cuff in a state where the biologic information detecting apparatus shown in the (A) is attached to a tragus.

A biologic information detecting apparatus of an eighth embodiment is obtained by providing the above-described biologic information detecting apparatus with, as shown in FIGS. 9(A) and 9(B), for example, a supporting member 57 in place of the sensor 33 shown in FIG. 1 and a cuff 56 in place of the sensor 34. The cuff 56 has therein a light emitting element 61 and a light receiving element 62. The cuff 56 further has an air pipe 36 for supplying air. FIG. 9(B) is an enlarged view of a portion of the supporting member 57 and the cuff 56 in a state where the biologic information detecting apparatus of FIG. 9(A) is attached to the tragus 1. To avoid complication of the drawings, the light emitting element 61 and the light receiving element 62 are not shown in the cuff 56 shown in FIG. 9(A). By providing the light emitting element and the light receiving element as a sensor in the cuff, biologic information of a living body part against which the cuff is pressed can be obtained.

In FIGS. 9(A) and 9(B), the supporting member 57 is provided for the first arm 31, and the cuff 56 is provided for the second arm 32. Alternatively, the supporting member 57 may be provided for the second arm 32 and the cuff 56 may be provided for the first arm 31.

The light emitting element 61 and the light receiving element 62 in the cuff 56 shown in FIG. 9(B) form a pulse wave detecting system of a reflection type and detect a pulse wave. In a process of detecting a pulse wave, by applying pressure to the tragus 1 by the cuff 56, a blood pressure can be also measured.

Ninth Embodiment

A biologic information detecting apparatus of a ninth embodiment has a pair of arms that face each other, a spindle connecting the pair of arms at one end of each of the pair of arms, a distance varying mechanism provided for the spindle and adjusting the interval between the other ends of the pair of arms, and a cuff for pressing a living body, attached to the other end of at least one of the pair of arms and on the facing side of the pair of arms. The arm to which the cuff is attached or a frame surrounding the cuff in a state where air is exhausted from the cuff is in contact with a living body. In a state where air is supplied to the cuff, the cuff comes into contact with the surface of a living body and presses a tragus.

Figure 10:
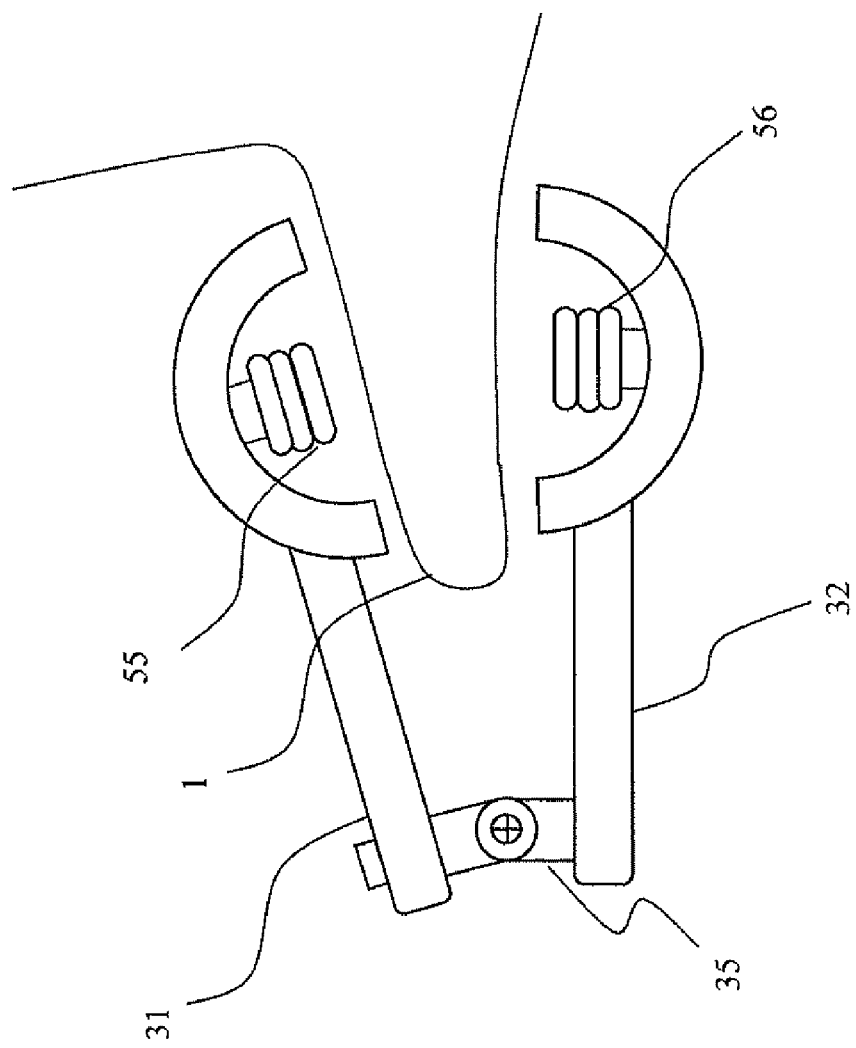
FIG. 10 is a diagram showing a configuration example of the biologic information detecting apparatus of the embodiment.

FIG. 10 shows a configuration example of a biologic information detecting apparatus of the ninth embodiment. Shown in FIG. 10 are a tragus 1, a first arm 31, a second arm 32, a spindle 35, a cuff 55, and a cuff 56. In FIG. 10, the cuff 55 is disposed on the inside of an arch- or bowl-shaped front end part of the first arm 31. The tragus 1 is not sandwiched by the cuff 55. The biologic information detecting apparatus is fixed to the surface position of the tragus with the front end part of the arm around the cuff 55. By supplying air to the cuff 55, the cuff 55 comes into contact with the surface of the tragus 1 and pressure is applied to the tragus 1.

With such a configuration, in a state where the air in the cuff is exhausted, the cuff surface is not in contact with the surface of the tragus, so that a region from which biologic information is to be obtained can be prevented from being pressed. Consequently, the cause of an error in measurement by pressurization to the surface of a tragus can be eliminated more than the method of fixing the biologic information detecting apparatus in a state where the cuff itself is in contact with the tragus from the beginning.

In FIG. 10, the cuff 55 is disposed in the first arm 31 and the cuff 56 is disposed in the second arm 32. A similar configuration can be obtained also in the case where a cuff is disposed only in one of the arms. Although the front end part of each of the first and second arms 31 and 32 has an arch- or bowl-shape in FIG. 10, the invention is not limited to the shapes. The shape may be a cylindrical shape, an angular cylindrical shape, a cone shape, or the like having therein a hollow. The shape of the arm is not limited to such shapes. A frame surrounding the cuff may be attached to the arm.

As described above, by constructing the biologic information detecting apparatus in such a manner that the arm to which the cuff is attached in a state where the air is exhausted from the cuff comes into contact with a tragus and, in a state where air is supplied to the cuff, the cuff comes into contact with the surface of the tragus and presses the tragus, the cause of a measurement error by pressurization to the cuff can be eliminated.

(Tenth Embodiment)

A biologic information detecting apparatus of a tenth embodiment has a pair of arms that face each other, a spindle connecting the pair of arms at one end of each of the pair of arms, a distance varying mechanism provided for the spindle and adjusting the interval between the other ends of the pair of arms, and cuffs for pressing a living body, attached to the other end of at least one of the pair of arms and on the facing side of the pair of arms. At least one of the cuffs can be detached from the arm to which the cuff is attached.

Figures 11A, 11B:
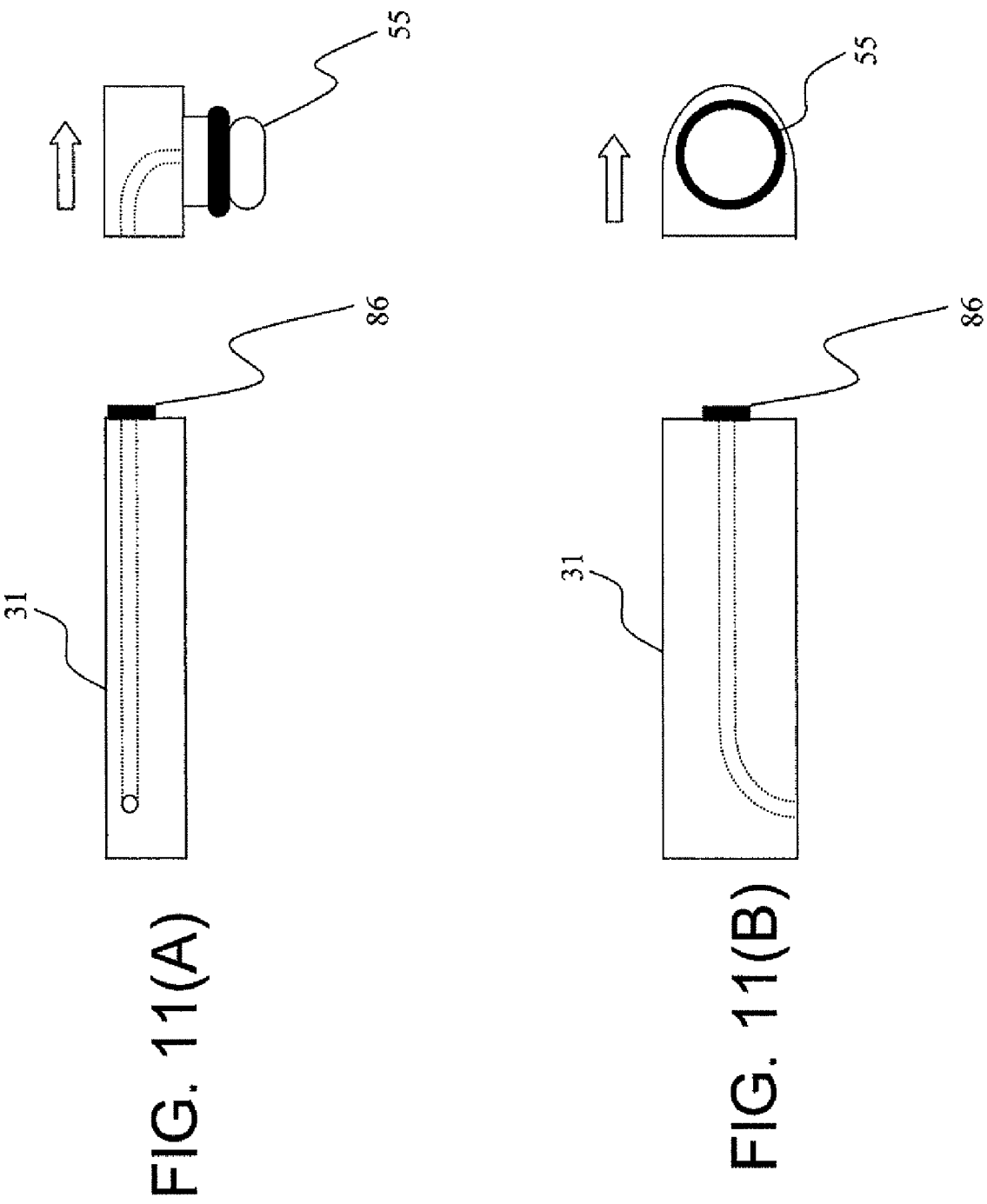
FIG. 11(A) is a front view showing a configuration example of the biologic information detecting apparatus of the embodiment.
FIG. 11(B) is a plan view showing a configuration example of the biologic information detecting apparatus of the invention.

FIG. 11(A) is a front view showing a configuration example of the biologic information detecting apparatus of the embodiment, and FIG. 11(B) is a plan view showing a configuration example of the biologic information detecting apparatus of the invention. Shown in FIGS. 11(A) and 11(B) are a first arm 31, a cuff 55, and a sealing member 86. In FIGS. 11(A) and 11(B), by pulling out the arm front end part having the cuff 55 in the direction of the arrow, the cuff can be replaced. In the case of the configuration example of the biologic information detecting apparatus shown in FIGS. 11(A) and 11(B), the sealing member 86 such as rubber packing or silicon has to be attached between the arm front end part and the arm body so as to prevent air leakage from a pipe for supplying/exhausting air to/from the cuff 55.

Figure 12A:
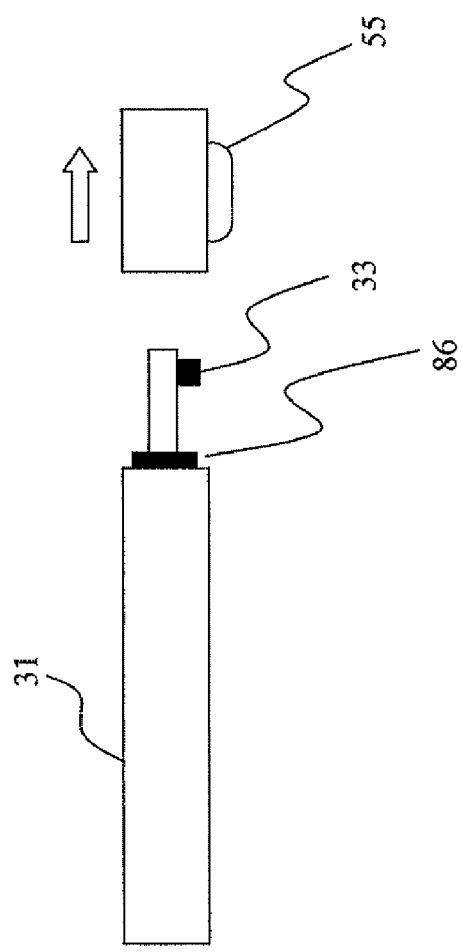
FIG. 12(A) is a front view showing a configuration example of the biologic information detecting apparatus of the embodiment.
Figure 12B:
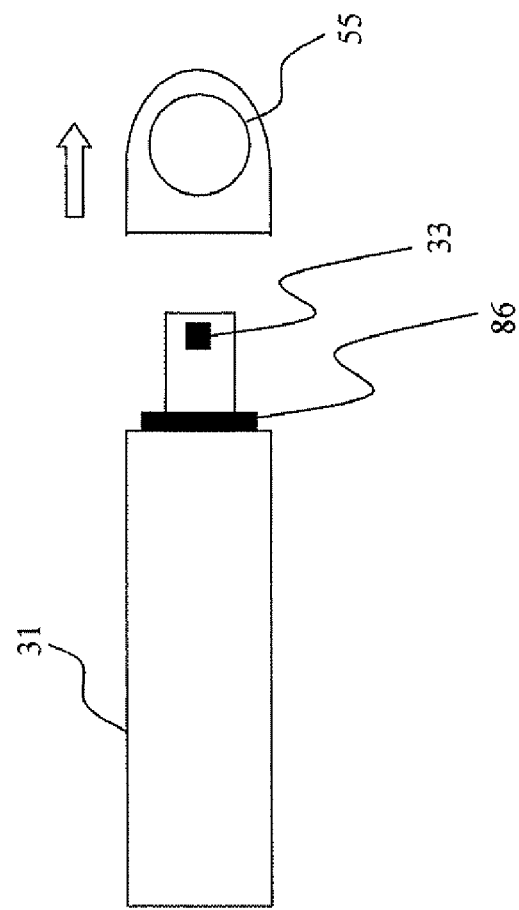
FIG. 12(B) is a plan view showing a configuration example of the biologic information detecting apparatus of the invention.

FIG. 12(A) is a front view showing another configuration example of the biologic information detecting apparatus of the embodiment, and FIG. 12(B) is a plan view showing another configuration example of the biologic information detecting apparatus of the invention. Shown in FIGS. 12(A) and 12(B) are a first arm 31, a sensor 33, a cuff 55, and a sealing member 86. In FIGS. 12(A) and 12(B), by pulling out the arm front end part having the cuff 55 in the direction of the arrow, the cuff can be replaced. In the case of the configuration example of the biologic information detecting apparatus shown in FIGS. 12(A) and 12(B), the cuff 55 has therein the sensor 33, and the sealing member 86 such as rubber packing or silicon has to be attached between the arm front end part and the arm body so as to prevent air leakage from a pipe for supplying/exhausting air to/from the cuff 55 and also from a supporting base of the sensor 33.

The cuff and the supporting mechanism which come into contact with the tragus tend to become dirty by ear wax, sebum, or the like and friction tends to occur, so that the cuff is formed so as to have a structure which can be easily detached from the arm. Consequently, by easily cleaning or replacing the dirty or damaged cuff, leakage of the cuff and decrease in permeability of the cuff can be prevented. By using a disposable cuff and a disposable supporting mechanism, an advantage is obtained such that sanitary management is facilitated.

(Eleventh Embodiment)

A biologic information detecting apparatus of an eleventh embodiment has a pair of arms that face each other, a spindle connecting the pair of arms at one end of each of the pair of arms, a distance varying mechanism provided for the spindle and adjusting the interval between the other ends of the pair of arms, and a cuff for pressing a living body, attached to the other end of at least one of the pair of arms and on the facing side of the pair of arms. The direction of coming into contact with the living body of at least one of the cuffs is variable.

Figure 13:
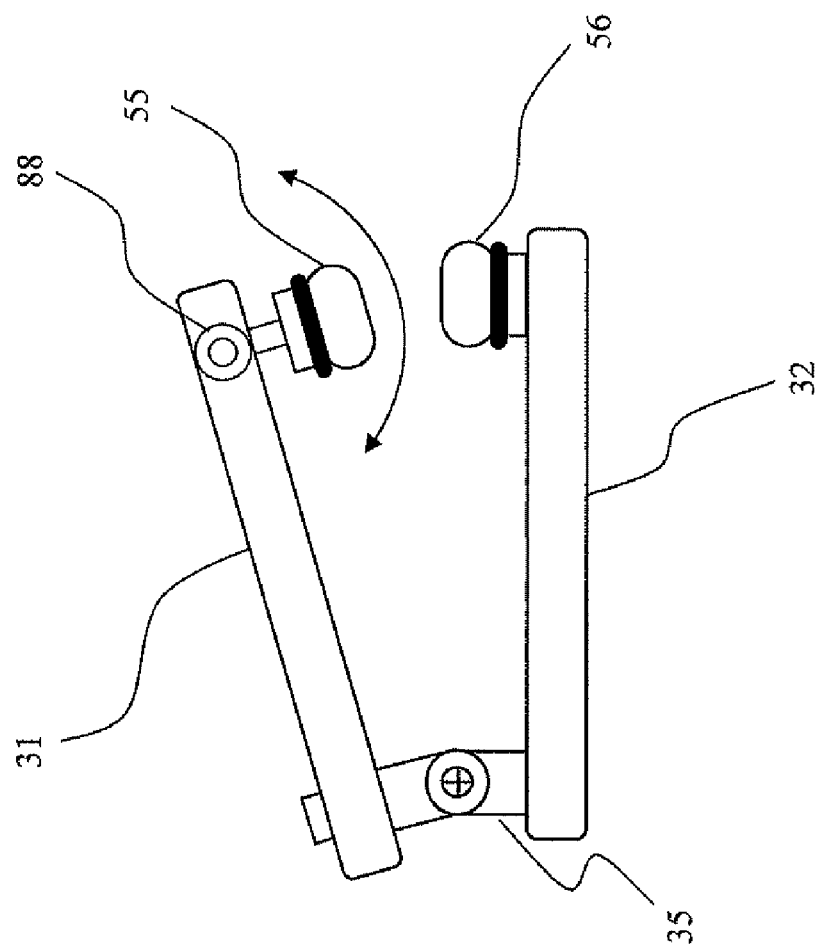
FIG. 13 is a diagram showing a configuration example of the biologic information detecting apparatus of the embodiment.

FIG. 13 shows a configuration example of the biologic information detecting apparatus of the embodiment. Shown in FIG. 13 are a first arm 31, a spindle 35, a cuff 55, a cuff 56, and a cuff rotating mechanism 88. In FIG. 13, the cuff rotating mechanism 88 capable of varying the direction in which the cuff 55 comes into contact with a tragus is provided. When the first arm 31 is an arm disposed on the outside of the tragus, the cuff 55 comes into contact with the outside of the tragus.

When the cuff 55 which comes into contact with the outside of the tragus has flexibility in rotation, by adjusting the distance between the cuffs to a length adapted to the shape of the tragus of the subject to a certain degree, without strictly adjusting the angle of the cuff, the rotation angle of the cuff 55 with respect to the tragus is determined so as to be along the shape of the tragus. Thus, easiness of attachment improves.

The cuff rotating mechanism 88 may have a structure capable of varying the direction contact with the tragus in one plane. By employing a structure capable of varying the direction contact with the tragus in two planes, it further facilitates contact of a cuff with a tragus.

Only the cuff 55 disposed in the first arm 31 is provided with the structure capable of varying the direction in FIG. 13. Alternatively, only the cuff 56 disposed in the second arm 32 may be provided with the structure capable of varying the direction or both of the cuffs 55 and 56 may be provided with the structure capable of varying the direction.

As described above, by providing the cuff disposed in the arm with the structure capable of varying the direction, attachment of the biologic information detecting apparatus to a tragus is facilitated. In particular, when the cuff which comes into contact with the outside of a tragus has flexibility in rotation, by adjusting the distance between the cuffs to a length adapted to the length of the tragus of the subject to a certain degree, without strictly adjusting the angle of the cuff, attachment of the apparatus to a tragus is facilitated.

(Twelfth Embodiment)

A biologic information detecting apparatus of a twelfth embodiment has a pair of arms that face each other, a spindle connecting the pair of arms at one end of each of the pair of arms, a distance varying mechanism provided for the spindle and adjusting the interval between the other ends of the pair of arms, and cuffs for pressing a living body, attached to the other end of at least one of the pair of arms and on the facing side of the pair of arms. At least one of the cuffs can slide in the long axis direction of the arm attached to the cuff.

When the first arm 31 is the arm disposed on the outside of a tragus, the cuff 55 comes into contact with the outside of the tragus.

Figure 14:
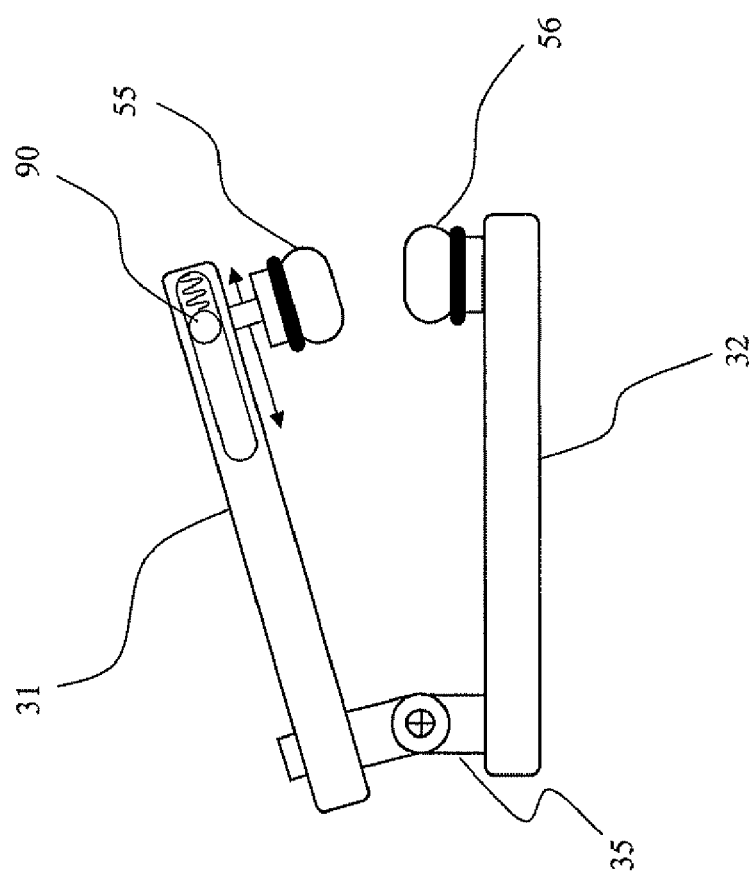
FIG. 14 is a diagram showing a configuration example of the biologic information detecting apparatus of the embodiment.

FIG. 14 shows a configuration example of the biologic information detecting apparatus of the embodiment. Shown in FIG. 14 are a first arm 31, a spindle 35, a cuff 55, a cuff 56, and a cuff sliding mechanism 90. In FIG. 14, the cuff 55 has the cuff sliding mechanism 90 which can slide in the long axis direction of the first arm 31. By changing the position of the cuff 55, the cuff 55 can come into contact with the optimum position in a tragus.

As shown in FIG. 14, by providing a spring for pulling the cuff 55 to the tip of the first arm 31, when the cuff 55 comes into contact with a tragus, the cuff 55 is positioned in a stable point. Alternatively, a spring for pushing the cuff 55 to the tip of the first arm 31 may be provided.

Although only the cuff 55 slides in FIG. 14, only the cuff 56 which comes into contact with inside of the tragus may slide, or both of the cuffs 55 and 56 may slide.

In FIG. 14, although the cuff 55 slides only in the long axis direction of the first arm 31, by employing a structure also capable of varying the direction in which the cuff 55 comes into contact with the tragus, contact with the optimum position in the tragus of the cuff 55 is further facilitated.

As described above, the interval between the other ends of the pair of arms can be adjusted by the distance varying mechanism provided for the spindle of the biologic information detecting apparatus and, by sliding the cuff, the cuff can be positioned in the optimum position in a living body.

(Thirteenth Embodiment)

A biologic information detecting apparatus of a thirteenth embodiment has an ear attachment for hanging the body of a biologic information detecting apparatus attached to an auricle of a human body from the base of the auricle of the human body, and a power supply unit for driving a sensor on the head side on the rear side of the auricle of the ear attachment. The apparatus may further include a pump for supplying/exhausting air to/from a cuff.

Figure 15:
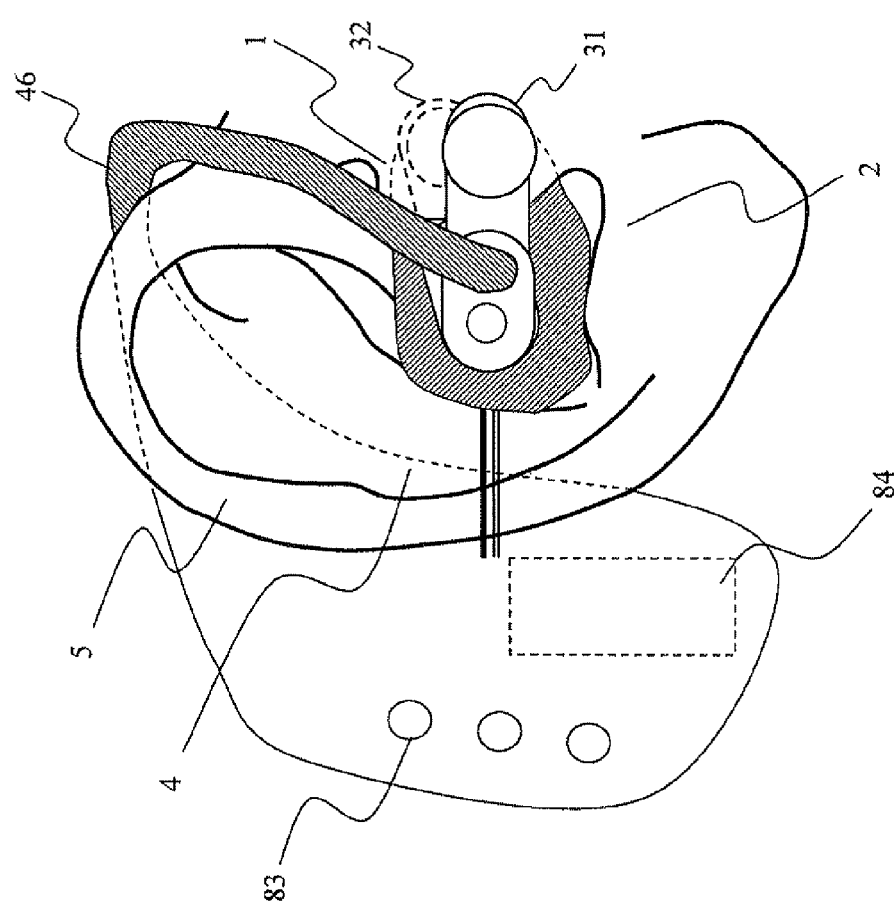
FIG. 15 is a diagram showing an attachment state of the biologic information detecting apparatus of the embodiment.

FIG. 15 shows an attachment state of the biologic information detecting apparatus of the embodiment. In the case of the configuration example of the biologic information detecting apparatus shown in FIG. 15, a pump 84 for supplying/exhausting air to/from a power supply unit (not shown) for driving a sensor and a cuff (not shown) is disposed in an ear attaching mechanism 46. Switches 83 may be also disposed.

The material and structure of a bridge are as same as described above.

By disposing the power supply unit in the ear attaching mechanism, portability and management of the biologic information detecting apparatus can be facilitated. By disposing the power supply unit in the ear attachment, a load on the arm is lessened, and noise caused by vibration in a wire can be reduced. By disposing the pump on the head, a pipe is easily fixed and noise which occurs at the time of detection of biologic information can be reduced.

The invention claimed is:

1. A biologic information detecting apparatus comprising:
    a pair of arms that face each other and are adapted to sandwich a projecting part of an auricle of a human body by a first arm disposed on a first side of the projecting part and a second arm disposed on a second side of the projecting part;
    a spindle connecting the arms at one end of each of the arms;
    a distance varying mechanism arranged on the spindle and adjusting an interval between the other ends of the arms;
    a cuff for pressing a living body, which is attached to the other end of at least one of the arms and attached on a facing side of the at least one of the arms; and
    a sensor for detecting biologic information, which is attached to the other end of at least one of the arms, characterized in that
    the biologic information is a blood pressure,
    the projecting part is a tragus,
    a front end part of the arm surrounding the cuff is adapted to press against a surface position of the tragus, and
    the cuff is adapted to not be in contact with the tragus in an air-exhausted state and, the cuff is adapted to be in contact with the tragus in an air-supplied state.

2. The biologic information detecting apparatus according to claim 1, further comprising a rotating mechanism for rotating at least one of the pair of arms around the spindle as a center axis.

3. The biologic information detecting apparatus according to claim 1, further comprising:
    a bridge adapted to extend across right and left auricles and to connect the arms to one of the right and left auricles and the other auricle to which the arms are not attached; and a power supply unit disposed in some midpoint of the bridge and driving the sensor.

4. The biologic information detecting apparatus according to claim 1, further comprising:

an ear attachment that is adapted to be placed around the base of the auricle; and a power supply unit disposed in the ear attachment.

* * * * *